United States Patent [19]

Medlen et al.

[11] Patent Number: 5,763,442
[45] Date of Patent: Jun. 9, 1998

[54] ANTI-PARASITIC ACTIVITY

[75] Inventors: Constance Elizabeth Medlen; Ronald Anderson, both of Pretoria, South Africa

[73] Assignee: Universiteit Van Pretoria, Gauteng, South Africa

[21] Appl. No.: 591,032

[22] Filed: Jan. 25, 1996

[30] Foreign Application Priority Data

Jan. 31, 1995 [ZA] South Africa ................... 95/0749

[51] Int. Cl.⁶ .................. A61K 31/495; A61K 31/50
[52] U.S. Cl. ........................................... 514/250
[58] Field of Search ............................... 514/250

[56] References Cited

U.S. PATENT DOCUMENTS

| | | | |
|---|---|---|---|
| 2,875,204 | 2/1959 | Barry et al. | 260/267 |
| 2,943,089 | 6/1960 | Barry et al. | 260/267 |
| 2,946,792 | 7/1960 | Barry et al. | 260/267 |
| 2,948,726 | 8/1960 | Barry et al. | 260/267 |
| 3,499,899 | 3/1970 | Girard et al. | 260/267 |
| 3,592,814 | 7/1971 | Barry et al. | 260/267 |
| 3,859,667 | 1/1975 | Lau et al. | 260/267 |

FOREIGN PATENT DOCUMENTS 0 374 991  6/1990  European Pat. Off. .

OTHER PUBLICATIONS

Van Rensburg, et al., Cancer Lett. (Shannon, Ireland), 1994, vol. 85, No. 1, pp. 59–63 Abstract Only.
Van Rensburg, et al., Int. J. Oncol., 1994, vol. 4, No. 5, pp. 1115–1119 Abstract Only.
Van Rensburg, et al., Int. J. Oncol., 1993, vol. 3, No. 5, pp. 1011–1013.
Anderson, et al., Biochem. Pharmacol., 1993, vol. 46, No. 11, pp. 2029–2038.
Krajewska, et al., Journ. Infect. Dis., 1993, vol. 167, No. 4, pp. 899–904.
Van Rensburg, et al., Cancer Res., 1993, vol. 53, No. 2, pp. 318–323.
Banerjee, et al. Chemotherapy, 1976, vol. 22, No. 3, pp. 242–252.
Il'yushonok et al., Teor. Eksp. Khim., 1977, vol. 13, No. 6, pp. 763–768 Abstract Only.
Ludwig, et al., Chem. Ber., 1982, vol. 115, No. 6, pp. 2380–2383 Abstract Only.
Kondratenko, et al., Teor. Eksp. Khim., 1977, vol. 13, No. 2, pp. 262–266 Abstract Only.
Ott et al., Monatsh. Chem., 1976, vol. 107, No. 4, pp. 879–888 Abstract Only.
Yoshida, et al., Waseda Daigaka Rikogaku Kenkyusho Hokoku, 1973, vol. 61, pp. 34–39.
Anderson, et al., Toxicol. Appl. Pharmacol., 1994, vol. 125, pp. 176–183.
Anderson, et al., Biochem. Pharmacol., 1988, vol. 37, No. 24, pp. 4635–4641.

Barry, et al., Leprosy Review, 1965, vol. 36, pp. 3–7.
Hagan, et al., Leprosy Review, 1979, vol. 50, pp. 129–134.
Franzblau et al., Antimicrobial Agents and Chemotherapy, 1989, vol. 33, No. 11, pp. 2004–2005.
Barry et al., 10G–Heterocyclic Compounds, 1958, vol. 53, p. 1959.
Sheagren, Journal of Parasitology, 1968, vol. 54, No. 6, pp. 1250–1251.
Mackey et al., British Journal of Dermatology, 1974, vol. 91, No. 1, pp. 93–96.
Vischer, Arzneimittel–Forschung (Drug Research), 1970, vol. 20, No. 5, pp. 714–723.
Evans et al., Annals of Tropical Medicine and Parasitology, 1989, vol. 83, No. 5, pp. 447–454.
Singh et al., Indian Journal of Experimental Biology, 1988, vol. 26, No. 1, pp. 48–52.
Mainguet et al., Acta Endoscopica, 1980, vol. 10, No. 4, pp. 307–313.
Arbiser et al., Journal of the American Academy of Dermatology, 1995, vol. 32, No. 21, pp. 241–247.
O'Connor et al., Biochemical Society Transactions, 1995, vol. 23, p. 357S.
O'Sullivan et al., J. Med. Chem., 1988, vol. 31, pp. 567–572.

*Primary Examiner*—Jerome D. Goldberg
*Attorney, Agent, or Firm*—G. Peter Nichols; Brinks Hofer Gilson & Lione

[57] ABSTRACT

The invention provides the use of a riminophenazine in the manufacture of a medicament to treat parasitic infections. The riminophenazine may be used for the prophylactic treatments of maleria or for the therapeutic treatment of maleria. A known anti-maleria drug, e.g. chloroquine or mefloquine may be administered as well. The riminophenazine may be a compound of the general formula:

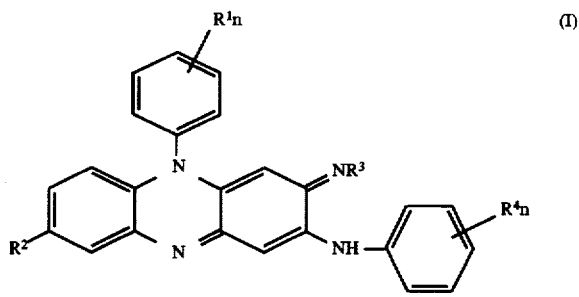

(I)

wherein:

$R^1$ is selected from hydrogen atoms, halogen atoms, alkyl, alkoxy and trifluoromethyl radicals, $R_2$ is selected from hydrogen or halogen atoms, $R^3$ is selected from hydrogen atoms, alkyl, substituted alkyl, cycloalkyl, cycloalkylalkyl, unsubstituted heterocyclic radicals, substituted heterocyclic radicals, unsubstituted heterocyclicalkyl and substituted heterocyclicalkyl radicals.

6 Claims, 2 Drawing Sheets

ANTI-PARASITIC ACTIVITY

TITLE OF THE INVENTION

THIS INVENTION relates to anti-parasitic activity, to therapeutic treatments and substances or compositions for use against parasites, and to the use of substances or compositions in the manufacture of medicaments for prophylactic or for therapeutic treatment against parasites.

BACKGROUND TO THE INVENTION

A problem in the therapy of diseases caused by parasites is that the parasites become resistant to drugs used for treating the patient. This resistance may be intrinsic or may be acquired. A major world problem arising in countries where maleria is prevalent is the growing resistance to the drugs which have been used for the prophylactic or therapeutic treatment of malaria.

BRIEF SUMMARY OF THE INVENTION

We have found that riminophenazines possess activity against diseases caused by parasites, eg. malaria. The present invention provides a substance or composition for use in the treatment of infections caused by parasites, said substance or composition comprising a riminophenazine. The substance or composition may be used for prophylactic and/or therapeutic treatment.

The invention also provides the use of a riminophenazine in the manufacture of a medicament to treat infections caused by parasites, e.g. malaria carried by flying insects such as mosquitos.

The invention further provides a method for the prophylactic and/or therapeutic treatment of infections of the human or animal body caused by parasites which comprises administering an effective amount of a riminophenazine to the human or animal body.

A riminophenazine is a phenazine containing a substituted imino substituent in one of the benzene rings. The imino group conveniently may be in the 2- (or 3-position depending on the nomenclature), the nitrogen atoms of the phenazine being in the 5- and 10-positions. Conveniently, there may also be an amino group in the same benzene ring as the imino group, preferably in the 3- (or 2-position, depending on the nomenclature). A presently preferred riminophenazine may have a 2-(substituted imino)-3-(substituted amino)-10-aryl grouping, (alternatively a 3-(substituted imino)-2-(substituted aMino)-10-aryl grouping, depending on the nomenclature used) optionally with a further substituent in the 7- or 8-position), i.e. a compound of the general formula:

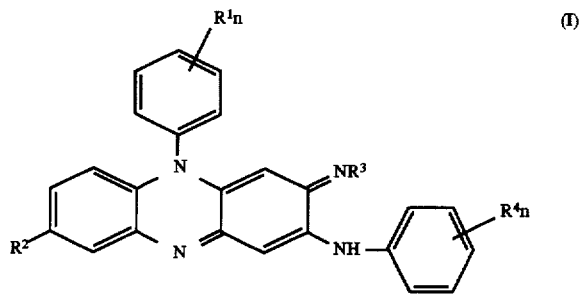

(I)

Following the nomenclature system used in chemical abstracts, such a compound would be known as a 7-($R^2$)-3-($R^4$n-anilino)-10-($R^1$n-phenyl)-2,10-dihydro-2-($R^3$-imino)-phenazine.

DETAILED DESCRIPTION OF THE INVENTION

Figure 1:
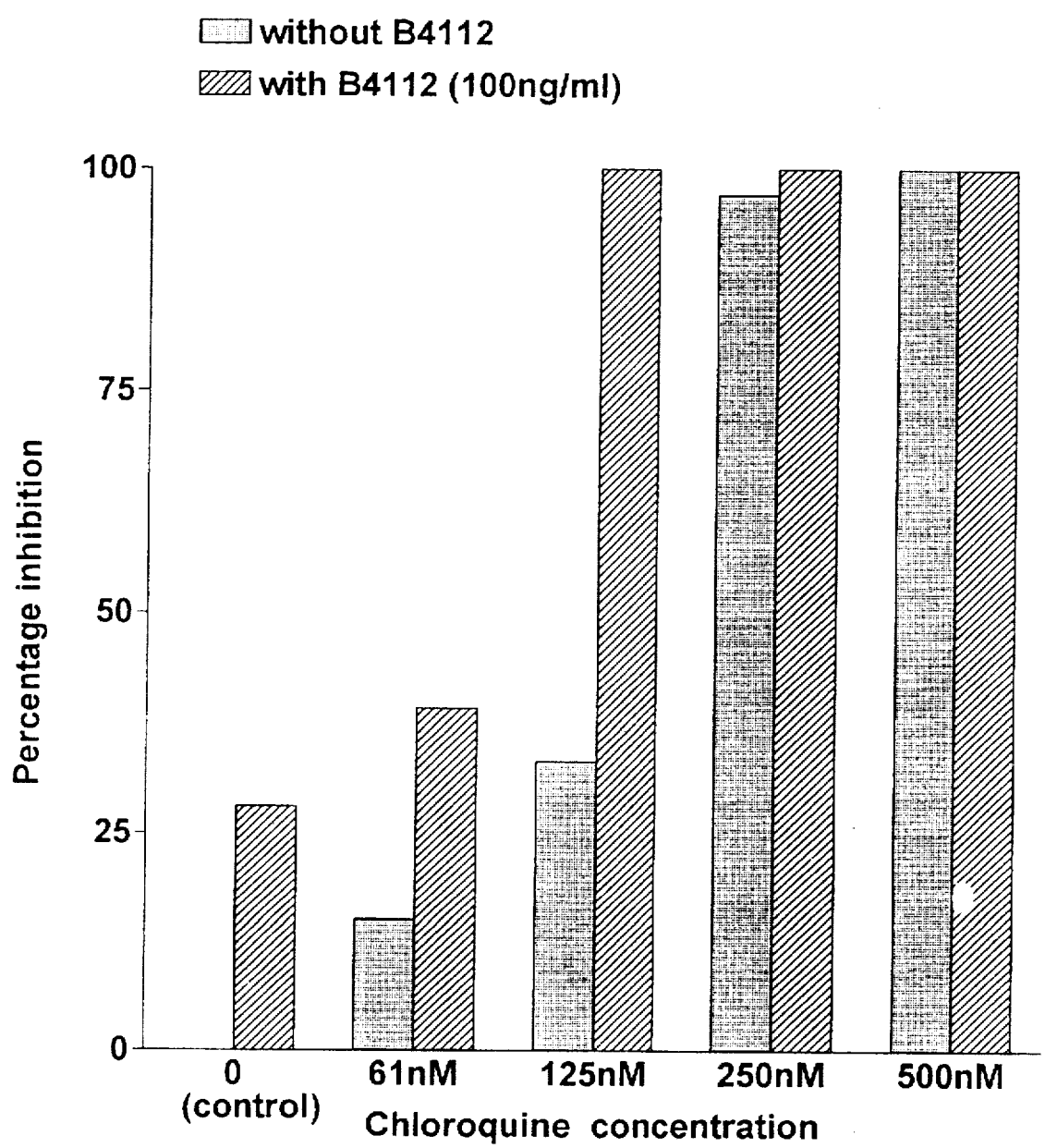

The riminophenazine may be used in the invention in the form of a pharmaceutically acceptable salt, e.g. an acid addition salt.

In general formula (I):

$R^1$ is a hydrogen atom, a halogen atom or an alkyl, alkoxy or trifluoromethyl radical, $R^2$ is a hydrogen or halogen atom, $R^3$ is selected from hydrogen, alkyl, substituted alkyl, cycloalkyl, cycloalkylalkyl, or is a substituted or unsubstituted heterocyclic or heterocyclicalkyl radical, $R^4$ is a hydrogen or halogen atom or an alkyl, alkoxy or trifluoromethyl radical, and n is 1, 2 or 3.

The radicals $R^1$ and $R^4$ may, for example, be hydrogen, chlorine, methyl, isopropyl, methoxy or trifluoromethyl. $R^1$ and $R^4$ may conveniently be in the 3- and/or 4-positions. When n is 2 or 3, there are two radicals $R^1$ and $R^4$ in the phenyl rings and these radicals may be the same or different. $R^2$ may conveniently be hydrogen or chlorine.

The radical $R^3$ in the above formula (I) may for example, be hydrogen, $C_1$-$C_4$-lower alkyl, (e.g. methyl, ethyl, n-propyl or isopropyl), cyclopropyl, cyclobutyl, cyclopentyl, cyclohexyl, cycloheptyl, methylcyclohexyl, hyroxycyclohexyl, cyclooctyl, cyclododecyl, N,N-dialkylaminoalkyl, cylohexylmethyl, piperidyl, alkyl-substituted piperidyl or benzyl substituted piperidyl.

A particularly convenient radical $R^3$ in the above formula (I) is a tetramethylpiperidyl (TMP) radical, e.g. a 4-TMP radical (i.e. 4-(2,2,6,6,-tetramethylpiperidyl) radical. Other preferred radicals for $R^3$, are cyclohexyl and N,N-diethylamino propyl radicals.

The compounds of general formula (I) may be used in a method of treatment of infections of the human or animal body caused by parasites, particularly malaria. The riminophenazines may be used for prophylactic and for therapeutic treatment of such infections.

The invention particularly provides the use of a compound of formula (I) in the manufacture of a medicament to treat infections caused by parasites, particularly malaria infections. The riminophenazines may be used alone or together with other compounds which have anti-parasitic activity. Such treatment may be by means of a single composition containing a riminophenazine and another anti-parasitic compound or by separate compositions, one containing a riminophenazine and the other containing another anti-parasitic compound.

Thus the invention also provides a pharmaceutical composition which comprises (a) a riminophenazine and (b) another anti-parasitic compound. A carrier or diluent may also be present.

Examples of anti-parasitic compounds are compounds which are used in the therapeutic treatment or prophylactic treatment of malaria, e.g. chloroquine, (i.e. the compound 7-Chloro-4-quinolinyl-N',N'-diethyl-1,4-pentanediamine) and mefloquine (i.e. the compound (R,S)(±)α-2-piperidinyl-2,8-bis(trifluoromethyl)-4-quinoline methanol hydrochloride.

Thus the invention particularly includes a pharmaceutical composition comprising a mixture of a riminophenazine and (a) chloroquine or mefloquine, together with a pharmaceutical carrier or diluent.

The compositions may be in any suitable form, e.g. a tablet, capsule, solution, sterile solution, or the like. They may be introduced orally, intravenously, transdermally, or in any other suitable manner. Typical compositions may contain from about 50 to 2000, more usually 100 to 600, e.g. 150 to 300 mg of active ingredient, together with one or more inert carriers. Any suitable carrier known in the art may be used. The riminophenazines may be administered to adults in daily dosages of from about 5 to 30 mg/kg per week, more usually 10 to 20 mg/kg per week for an average adult for prophylactic purposes. For therapeutic treatment, the dosage can be increased substantially, e.g. to amounts of from 100 to 200 mg per day.

The riminophenazine in the composition preferably is of the above general formula (I) in which $R^1$, $R^2$, $R^3$, $R^4$ and n have the meanings given above.

Presently preferred examples of $R^1$ and $R^4$ in the above formula (I) are hydrogen, chlorine, methyl and trifluoromethyl. Presently preferred examples of $R^2$ are hydrogen and chlorine. Presently preferred examples of $R^3$ are TMP, piperidyl, hydrogen, alkyl, cycloalkyl, dialkylaminoalkyl and alkylcycloalkyl.

Many of the riminophenazines of the above general formula (I) are known compounds whose preparation has been described in the literature, e.g. including South African Patents Nos. 57/1249 and 57/3266. Alternatively other general methods of preparation described in the literature for the preparation of riminophenazines may be followed.

For example a 1-anilino-2-nitrobenzene of general formula (II) may be reduced, e.g. with hydrogen in the presence of a palladium carbon catalyst, or in zinc and acetic acid, to form the corresponding 1-anilino-2-aminobenzene (i.e. 2-amino-diphenylamine) of general formula (III), in which $R^1$, $R^2$ and n have the meanings defined above. Heating at temperature of 40°–55° C. can be used.

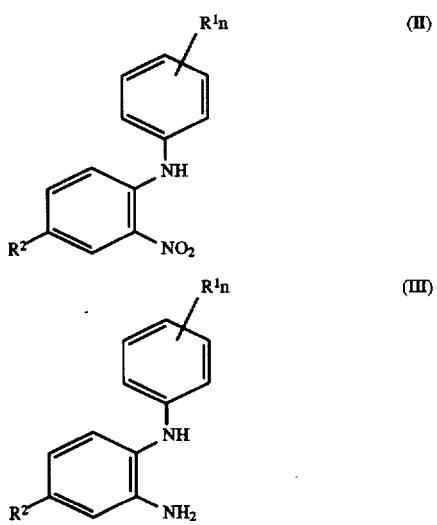

The diphenylamine of formula (III) may be oxidatively condensed, e.g. with ferric chloride and concentrated hydrochloric acid or acetic acid to form a riminophenazine of general formula (IV), i.e. a compound of formula (I) in which $R^3$ is hydrogen. Ethyl alcohol may be used as a solvent. Stirring at ambient temperatures of, preferably, below 15° C. may be used.

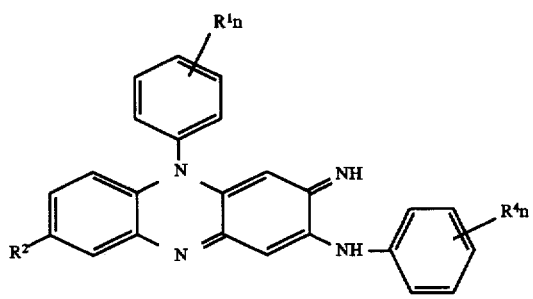

The other riminophenazines of general formula (I) can be formed from the riminophenazine of general formula (IV) by reaction with an amine of formula $R^3$-$NH_2$. Refluxing of the reactants, in solution in dioxane, for a period of 3 to 5 hours may be necessary.

The 1-anilino-2-nitrobenzene starting material may be prepared by reacting a 2-halo-nitrobenzene containing a $R^2$-radical in the 5-position, with a formulated aniline having a $R^1$ substituent in the phenyl ring. The reaction may be carried out in the presence of anhydrous potassium carbonate and while boiling the reactants in dimethylformamide.

Particular examples of compounds of general formula (I) are set out in the following Table I:

TABLE 1

| Compound | $R^1$ | $R^2$ | $R^3$ | $R^4$ |
|---|---|---|---|---|
| B283 | H | H | H | H |
| B628 | 4-Cl | H | H | H |
| Clofazimine (B663) | 4-Cl | H | —CH(CH$_3$)$_2$ | 4-Cl |
| B669 | H | H | —Cyclohexyl | H |
| B670 | H | H | —CH(CH$_3$)2 | H |
| B673 | 4-Cl | H | Cyclohexyl | 4-Cl |
| B718 | H | H | —C$_2$H$_5$ | H |
| B729 | H | H | Cycloheptyl | H |
| B741 | 4-Cl | H | 4-methyl cyclohexyl | 4-Cl |
| B746 | 4-Cl | H | —C$_2$H$_5$ | 4-Cl |
| B749 | 4-Cl | H | —(CH$_2$)$_2$N.(C$_2$H$_5$)$_2$ | 4-Cl |
| B759 | 4-Cl | H | —(CH$_2$)$_3$CH$_3$ | 4-Cl |
| B796 | H | H | -cyclopentyl | H |
| B980 | 4-F | H | —CH(CH$_3$)$_2$ | 4-F |
| B1865 | H | Cl | —CH(CH$_3$)$_2$ | H |
| B1912 | H | Cl | -cyclohexyl | H |
| B3677 | 4-me | H | -cyclohexyl | 4-me |
| B3763 | H | H | -cyclohexyl methyl | H |
| B3779 | 4-Cl | H | 4-(N,N-diethylamino)- -2-methyl-butyl | 4-Cl |
| B3786 | Cl | H | 4'-TMP | Cl |
| B3825 | 4-Cl | H | 4-hydroxy cyclohexyl | 4-Cl |
| B3962 | H | H | 4'-TMP | H |
| B4019 | H | Cl | 4'-TMP | H |
| B4021 | H | Cl | —C$_2$H$_5$ | H |
| B4070 | 4-me | H | -4-piperidyl | 4-me |
| B4090 | 4-Cl | Cl | 4'-TMP | 4-Cl |
| B4100 | 3,4-di-Cl | H | 4'-TMP | 3,4-di-Cl |
| B4103 | 4-CF$_3$ | H | 4'-TMP | 4-CF$_3$ |
| B4104 | 4-Cl | Cl | Cyclohexyl | 4-Cl |
| B4112 | 3-Cl | H | 4'-TMP | 3-Cl |
| B4121 | 3,5-di-Cl | H | 4'-TMP | 3,5-di-Cl |
| B4123 | 3-Cl | Cl | 4'-TMP | 3-Cl |
| B4126 | 3-CF$_3$ | H | 4'-TMP | 3-CF$_3$ |
| B4127 | 3-CF$_3$ | Cl | 4'-TMP | 3-CF$_3$ |
| B4128 | 2,4-di-Cl | H | 4'-TMP | 2,4-di-Cl |
| B4154 | 3,4-di-Cl | H | —(CH$_2$)$_3$N.(C$_2$H$_5$)$_2$ | 3,4-di-Cl |
| B4158 | 4-CH(CH$_3$)$_2$ | H | 4'-TMP | 4-CH(CH$_3$)$_2$ |
| B4159 | 4-CH(CH$_3$)$_2$ | Cl | 4'-TMP | 4-CH(CH$_3$)$_2$ |
| B4163 | 3-CF$_3$-4-Cl | H | 4'-TMP | 3-CF$_3$-4-Cl |
| B4166 | H | H | -cyclooctyl | H |
| B4169 | 3,4,5-tri-Cl | H | 4'-TMP | 3,4,5-tri-Cl |
| B4170 | H | H | -cyclopropyl | H |
| B4171 | H | H | -cyclododecyl | H |
| B4172 | H | H | -cyclobutyl | H |
| B4173 | H | H | 4'-(N-benzylpiperidyl) | H |
| B4174 | 4-OCH$_3$ | H | 4'-TMP | 4-OCH$_3$ |
| B4175 | 3,4-di-Cl | H | Cyclohexyl | 3,4-di-Cl |
| B4177 | 4-OCF$_3$ | H | 4'-TMP | 4-OCF$_3$ |

In the above table, when $R^3$ is 4'-TMP, the TMP radical is a 4-(2,2,6,6,-tetramethyl piperidine) radical, and me is used as an abbreviation for methyl.

The chemical names for some of the compounds of Table I are set out in Table II below:

TABLE II

| | |
|---|---|
| B663 - | N,5-bis-(4-chlorophenyl)-3,5-dihydro-3-[(1-methylethyl)imino]-2-phenazinamine; |
| B669 - | N,5-bis(phenyl)-3,5-dihydro-3-(cyclohexylimino)-2-phenazinamine; |
| B796 - | N,5-bis-phenyl-3,5-dihydro-3-(cyclopentylimino)-2-phenazinamine; |
| B3677 - | N,5-bis(4-methylphenyl)-3,5-dihydro-3-(cyclohexylimino)-2-phenazinamine; |
| B3763 - | N,5-bis(phenyl)-3,5-dihydro-3-[(cyclohexylmethyl)imino]-2-phenazinamine; |
| B3779 - | N,5-bis(4-chlorophenyl)-3,5-dihydro-3-[(4-diethylamino-2-methylbutyl)imino]-2-phenazinamine; |
| B3962 - | N,5-bis(phenyl)-3,5-dihydro-3-[(2',2',6',6'-tetramethyl-4-piperidyl)imino]-2-phenazinamine; |
| B4070 - | N,5-bis(4-methylphenyl)-3,5-dihydro-3-[(4-piperidyl)imino]-2-phenazinamine; |
| B4100 - | N,5-bis(3,4-dichlorophenyl)-3,5-dihydro-3-[(2',2',6',6'-tetramethyl-4-piperidyl)-imino]-2-phenazinamine; |
| B4103 - | N,5-bis(4-trifluoromethylphenyl)-3,5-dihydro-3[(2',2',6',6'-tetramethyl-4-piperidyl)imino]-2-phenazinamine; |
| B4104 - | N,5-bis(4-chlorophenyl)-8-chloro-3,5-dihydro-3-(cyclohexylimino)-2-phenazinamine; |
| B4112 - | N,5-bis(3-chlorophenyl)-3,5-dihydro-3-[(2',2',6',6'-tetramethyl-4-piperidyl)-imino]-2-phenazinamine; |
| B4121 - | N,5-bis(3,5-dichlorophenyl)-3,5-dihydro-3-[(2',2',6',6'-tetramethyl-4-piperidyl)-imino]-2-phenazinamine; |
| B4123 - | N,5-bis(3-chlorophenyl)-8-chloro-3,5-dihydro-3[(2',2',6',6'-tetramethyl-4-piperidyl)-]-2-phenazinamine; |
| B4126 - | N,5-bis(3-trifluoromethyl-4-phenyl)-3,5-dihydro-3-[(2',2',6',6'-tetramethyl-4-piperidyl)-imino]-2-phenazinamine; |
| B4127 - | N,5-bis(3-trifluoromethylphenyl)-8-chloro-3,5 dihydro-3-[(2',2',6',6'-tetramethyl-4-piperidyl) imino]-2-phenazinamine; |
| B4154 - | N,5-bis(3,4-di-chlorophenyl)-3,5-dihydro-3-[(3'-(N,N-diethylamino)-propylimino]-2-phenazinamine; |
| B4158 - | N,5-bis(4-isopropylphenyl)-3,5-dihydro-3-[(2',2',6',6'-tetramethyl-4-piperidyl)-imino]-2-phenazinamine; |
| B4159 - | N,5-bis(4-isopropylphenyl)-8-chloro-3,5-dihydro-3-[(2',2',6',6'-tetramethyl-4-piperidyl)-imino]-2-phenazinamine; |
| B4163 - | N,5-bis[(3-trifluoromethyl)-4-chlorophenyl]-3,5-dihydro-3-[(2',2',6',6'-tetramethylpiperidyl)-imino]-2-phenazinamine |
| B4166 - | N,5-bis(phenyl)-3,5-dihydro-3-(cyclooctylimino)-2-phenazinamine; |
| B4169 - | N,5-bis(3,4,5-tri-chlorophenyl)-3,5-dihydro-3[(2',2',6',6'-tetramethyl-4-piperidyl)-imino]-2-phenazinamine; |
| B4170 - | N,5-bis(phenyl)-3,5-dihydro-3-(cyclopropylimino)-2-phenazinamine; |
| B4171 - | N,5-bis(phenyl)-3,5-dihydro-3-(cyclododecylimino)-2-phenazinamine; |
| B4172 - | N,5-bis(phenyl)-3,5-dihydro-3-(cyclobutylimino)-2-phenazinamine; |
| B4173 - | N,5-bis(phenyl)-3,5-dihydro-3-[4'-(N-benzylpiperidyl)-imino]-2-phenazinamine; |
| B4174 - | N,5-bis(4-methoxyphenyl)-3,5-dihydro-3-[(2',2',6',6'-tetramethyl-4-piperidyl)-imino]-2-phenazinamine; |
| B4175 - | N,5-bis(3,4-di-chlorophenyl)-3,5-dihydro-3-(cyclohexylimino)-2-phenazinamine. |

Treatment of parasite-infected human erythrocytes with a compound of the above general formula (I) results in the reduction of resistance of the parasite to anti-parasitic compounds, and/or in anti-parasitic activity, particularly anti-malarial activity. Furthermore, treatment of non-infected humans with a compound of the above general formula (I) results in protection against infection by parasites.

Without being bound by theory, the possible reasons for the surprising activity of the compounds of formula (I) is that a relationship may exist between riminophenazine mediated enhancement of $PLA_2$ (i.e. phospholipose $A_2$) activity and the inhibition of ATPase of P-glycoprotein, or the inhibition of P-glycoprotein activity may occur as a secondary consequence of the depletion of cellular ATP following prolonged inhibition of $Na^+$, $K^+$, ATPase activity. Thus, a reversal of resistance to anti-parasitic agents may occur, primarily via activation of $PLA_2$ and consequent lysophospholipid-mediated inhibition of the ATPase activity of P-glycoprotein. Both of these mechanisms may be operative.

The riminophenazines of the above formula (I), contain an imino group. They are reasonably non-toxic and possess a potent resistant modifying activity when administered in vitro. We have found that they inactivate the drug pump activity in cell lines with acquired multi-drug resistance.

In addition to being relatively non-toxic, the compounds of the above general formula (I) are non-carcinogenic and non-myelosuppressive. They possess direct antineoplastic activity as well as multi-drug resistance modifying potential.

DESCRIPTION OF PREFERRED EMBODIMENTS, AND THE DRAWINGS

Particular riminophenazines which have shown good activity against the maleria microorganism Plasmodium falciparium are B4112, namely N,5-bis(3-chlorophenyl)-3,5-dihydro-3-(4'-TMP-imino)-2-phenazinamine, B4158, namely N,5-bis(4isoprophylpenyl)-3,5-dihydro-3-(4'-TMP-imino)-2-phenazinamine, B4121, namely N,4-bis(3,5-dichlorophenyl)-3,5-dihydro-3-(4'-TMP-imino)-2-phenazinamine, B4100, namely N,5-bis(3,4-dichlorophenyl)-3,5-dihydro-3-(4'-TMP-imino)-2-phenazinamine and B669, namely N,5-bis(phenyl)-3,5-dihydro-3-(cyclohexylimino)-2-phenazinamine.

Figure 2:
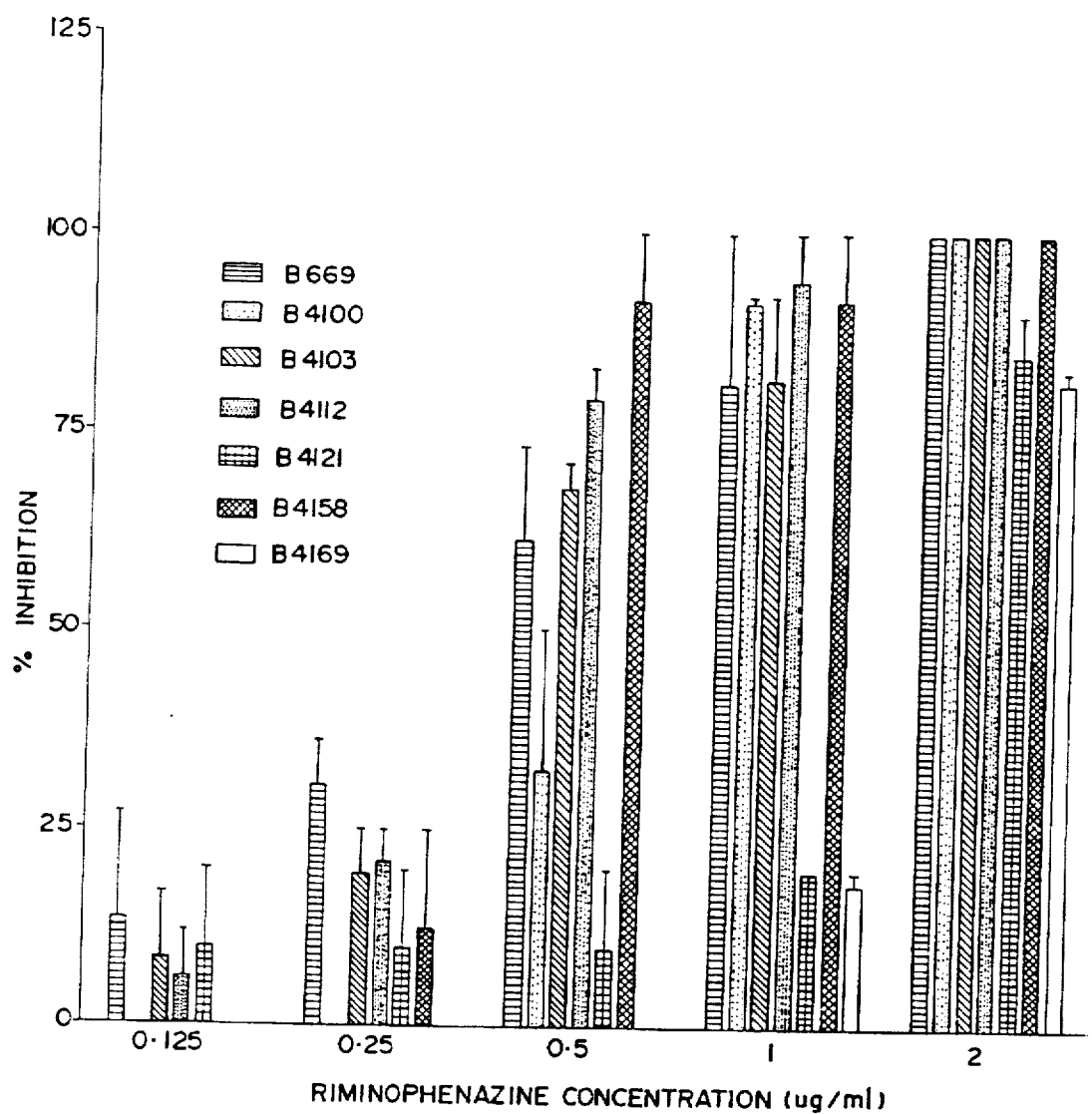

Certain of the results of experiments given in the Examples, below, are illustrated in the accompanying drawings in which FIG. 1 is a graph of the percentage inhibition of Plasmodium falciparum resistance against chloroquine concentration, for the experiment described in Example 3; and FIG. 2 is a graph of the percentage inhibition of Plasmodium falciparum resistance against riminophenazine concentration for the experiment described in Example 4. It shows the direct anti-material activity of the riminophenazines used in that Example.

The invention is illustrated in non-limiting manner by reference to the following Examples.

Example 1

THE REVERSAL OF CHLOROQUINE RESISTANCE OF *PLASMODIUM fALCIPARUM* BY B669

B669 is the compound N,5-bis-(phenyl)-3,5-dihydro-3-(cyclohexylimino)-phenazinamine.

Resistance to chloroquine by malaria parasites can be mediated by a type of P-glycoprotein homologue termed Pg H1 which is similar to the mammalian drug afflux pump (MDR-I present in multi-drug resistant cancer cell lines). This type of resistance can be reversed by the calcium channel blocker, verapamil. The dose of this calcium channel blocker required to reverse this type of resistance in vitro would, however, cause severe side effects in vivo.

The activity of riminophenazines to reverse chloroquine resistance in Plasmodium falciparum was tested in the following manner:

Methods

A preliminary series of experiments were carried out using two laboratory strains of *P. falciparum* (RB-1 and Fab-9). These strains were obtained from the Medical Research Council, Durban, where they were characterised as being either mildly resistant or sensitive to chloroquine. The isolates were maintained in suspension culture in known manner (as described by Freese J A, Markus M B and Golenser J, 1991; *Bulletin of the World Health Organization* 69: 707–712).

Infected erythrocytes were diluted with human O-positive red blood cells to a parasitaemia of 0.2–0.9% and suspended to 3% in RPMI containing 44 mg/l hypoxanthine and 10% human type O serum. Aliquots (100 μl) of the suspension were dispensed into the wells of 96-well microtitre plates. To these suspensions 100 μl of the medium were added containing either chloroquine or B669 alone or in combination. The final drug concentrations were 31, 62, 125, 250 500 and 1000 nM for chloroquine and 0.125, 0.25, 0.5 and 1.0 μg/ml for B669. Relevant solvent controls were included. The plates were incubated for 24 hours at 38° C. in a desiccator gassed with 5% $O_2$, 5% $CO_2$ and 90% $N_2$. Thin blood smears were prepared from each well, stained with Giemsa stain and the percentage of red blood cells infected by at least one parasite determined microscopically.

Results

The solvent systems had no effect on the percentages of infected cells. B669 alone had a direct effect on both strains at 1.0 μg/ml. Although the percentage parasitaemia did not differ from the untreated control systems, a morphological deterioration of the parasites was observed at this concentration (as set out in Table 1 below). The experimental agent (B669) however, did not increase the sensitivity of the chloroquine sensitive strain to chloroquine (Table 1) whereas, in the case of the chloroquine resistant strain sensitivity to 500 nM chloroquine was increased up to three fold in the presence of 0.25 μg/ml B669 (see Table 2 below) and up to two fold to 125 nM chloroquine in the presence of 0.125 μg/ml B669. In the tables, nd means not determined.

Conclusion

The results of this study indicated the potential use of the riminophenazines in the treatment of, or prophylaxis against chloroquine resistant malaria.

TABLE 1

The effect of B669 on the sensitivity to chloroquine of a chloroquine sensitive strain of *Plasmodium falciparum* (Fab-9)

| B669 Treatment (μg/ml) | Percentage red blood cells infected with *P. falciparum* (Fab-9) after Chloroquine treatment (nM): | | | | | | |
|---|---|---|---|---|---|---|---|
| | 0 | 31 | 62 | 125 | 250 | 500 | 1000 |
| 0 | 3.8 | 4.9 | 3.9 | 2.4* | 3.1* | 0.1* | 0 |
| 0.125 | 4.0 | 3.9 | nd | nd | nd | 0.9 | nd |
| 0.25 | 4.4 | 3.1 | nd | 2.9 | nd | 0.1* | nd |
| 0.5 | 3.0 | 2.7* | nd | 3.0 | nd | 0.1* | nd |
| 1.0 | 4.1* | 2.9 | nd | 0.9 | nd | 0.1* | nd |

*parasites morphologically abnormal

TABLE 2

The effect of B669 on the sensitivity to chloroquine of a chloroquine resistant strain of *Plasmodium falciparum* (RB-1)

| B669 Treatment (μg/ml) | Percentage red blood cells infected with *P. falciparum* (RB-1) after Chloroquine treatment (nM): | | | | | | |
|---|---|---|---|---|---|---|---|
| | 0 | 31 | 62 | 125 | 250 | 500 | 1000 |
| 0 | 3.5 | 3.5 | 3.3 | 3.3 | 3.1 | 3.0 | 0.4 |
| 0.125 | 3.6 | nd | nd | 1.6* | nd | 1.3 | nd |
| 0.25 | 4.0 | 3.9 | 2.8* | 1.9* | nd | 0.9* | 0 |
| 0.5 | 3.2 | nd | nd | nd | 1.4* | nd | 0.1 |
| 1.0 | 2.6* | 2.6* | nd | nd | 0.1* | nd | 0 |

*parasites morphologically abnormal

Example 2

THE REVERSAL OF CHLOROQUINE RESISTANCE OF *PLASMODIUM fALCIPARUM* BY B669

The following experiment was done to confirm previous results which were obtained microscopically and details of which are set out in Example 1.

Methods

For this experiment the same two strains of *P. falciparum*, as used in Example 1 (RB-1 and Fab-9) were again used. Infected erythrocytes were diluted with human O-positive red blood cells to a parasitaemia of 0.2–0.9% and suspended to 3% in RPMI containing 44 mg/l hypxanthine and 10% human type serum. Aliquots (100 μl) of the suspension were dispensed into the wells of 96-well microtitre plates. To these suspensions 100 μl of the medium were added containing either chloroquine or B669 alone or a combination of chloroquine and B669. Relevant solvent controls were included. Negative control wells were also included containing uninfected red blood cells. The plates were incubated at 38° C. in a desiccator gassed with 5% $O_2$, 5% $CO_2$ and 90% $N_2$. After 24 hours 100 μl culture medium of each well was replaced with 100 ml of hypoxathine—free medium containing 10% human serum and 0.5μ $Ci^3H$-hypoxanthine and incubated for a further 18 hours. The contents of the wells were then harvested on to glass fibre filters. The filters were washed with distilled water, dried, haemoglobin dissolved in a sodium bicarbonate solution and placed in scintillation vials containing 4 ml scintillation fluid and counted for 5 min in a liquid scintillation counter.

Results

The percentage inhibition was calculated as follows:

Percentage inhibition =

$$100 - \frac{CPM \text{ (drug treated cells)} - CPM \text{ (neg. control)} \times 100}{CPM \text{ (untreated cells)} - CPM \text{ (neg. control)}}$$

where CPM was the mean of two values of counts per minute for each treatment. The percentage inhibition is shown in the following Tables.

TABLE 3

The effect of B669 on the sensitivity to chloroquine of a chloroquine sensitive strain of *Plasmodium falciparum* (Fab-9) using the $^3$H-hypoxanthine uptake method

| B669 Treatment | PERCENTAGE INHIBITION CHLOROQUINE TREATMENT (nM) | | | | | | |
|---|---|---|---|---|---|---|---|
| (μg/ml) | 0 | 31 | 62 | 125 | 250 | 500 | 1000 |
| 0 | 0 | 52.5 | 23.5 | 48.7 | 66.9 | 100 | 100 |
| 0.125 | 29.8 | 12.9 | 7.4 | 68.3 | 81.4 | 100 | 100 |
| 0.25 | 10.4 | 21.0 | 0 | 34.9 | 85.5 | 100 | 100 |
| 0.5 | 41.7 | 60.5 | 91.7 | 93.6 | 100 | 100 | 100 |
| 1.0 | 46.6 | 98.8 | 95.9 | 100 | 100 | 100 | 100 |

TABLE 4

The effect of B669 on the sensitivity to chloroquine of a chloroquine sensitive strain of *Plasmodium falciparum* (RB-9) using the $^3$H-hypoxanthine uptake method

| B669 Treatment | PERCENTAGE INHIBITION CHLOROQUINE TREATMENT (nM) | | | | | | |
|---|---|---|---|---|---|---|---|
| (μg/ml) | 0 | 31 | 62 | 125 | 250 | 500 | 1000 |
| 0 | 0 | 0 | 0 | 8 | 33 | 100 | 100 |
| 0.125 | 0 | 15.2 | 12.2 | 0 | 100 | 100 | 100 |
| 0.25 | 0 | 0 | 26.4 | 0 | 100 | 98.8 | 95 |
| 0.5 | 0 | 0 | 16.6 | 92 | 95 | 100 | 100 |
| 1.0 | 0 | 58.6 | 100 | 100 | 100 | 100 | 100 |

The solvent systems had no effect on the percentages of infected cells. As can be seen from Table 3, only the chloroquine sensitive strain (RB-1) was sensitive to B669 alone (0.125–1.0 μg/ml) while the experimental agent (B669) did not increase the sensitivity of this strain to chloroquine. As can be seen from Table 3, in the case of the chloroquine resistant strain sensitivity to 250 nM chloroquine was increased up to three fold in the presence of 0.125–0.5 μg/ml B669 and sensitivity to 125 μM chloroquine up to ten fold in the presence of 0.5 and 1.0 μg/ml B669. Effects of the experimental drug was also seen at concentrations of chloroquine as low as 31 and 62 nM.

Discussion

These results, as well as the results obtained with the microscopy method of Example 1 indicate the ability of riminophenazines to reverse chloroquine resistance in malaria. Direct anti-malaria activity, especially in the case of the chloroquine sensitive strain of *P. falciparum*, was also possessed by B669.

Example 3

THE REVERSAL OF CHLOROQUINE RESISTANCE IN *PLASMODIUM fALCIPARUM* BY B4112

To test the activity of B4112 to reverse chloroquine resistance in *Plasmodium falciparum*, the following experiment was done:

Methods

A chloroquine resistant strain of *P. falciparum* (FAC 8) was obtained from Dr P Smith, University of Cape Town (originally from Dr A F Cowman, Royal Melbourne Hospital, Victoria, Australia).

Malaria infected erythrocytes (ring stage) were diluted with human O-positive red blood cells together with RPMI containing 44 mg/l hypoxanthine and 10% human type A serum to a parasitaemia of 2% and a haematocrit of 5%. This suspension was incubated in a gassed desiccator (5% $O_2$, 5% $CO_2$ and 90% $N_2$) with serial dilutions of chloroquine ranging from 61–500 nM in 96-well microtitre culture plates for 48 hours in the presence or absence of a fixed concentration of B4112 (100 ng/ml). Relevant solvent controls were included.

At the end of the incubation period, 100 μl of the medium was removed from each well and replaced with a fixation solution containing 10 mM TRIS, 10 mM Na-Azide and 150 mM Na Cl. The plates were stored overnight at 4° C. and then 25 μl aliquots from each well were stained in test tubes with 0.5 ml thiazole orange at a concentration of 0.25 μg/ml in phosphate-buffered saline (PBS). After an incubation period of 1 hour at room temperature (in the dark), the tubes were placed on ice and the level of parasitaemia determined by flow cytometry using a Coulter Epics Profile II (Coulter Electronics Ltd, Hialeah, PLA, USA).

Results

The solvent systems had no effect on the percentages of infected cells. Chloroquine per se inhibited the growth of the parasite at concentrations ≧250 nM (FIG. 1), whereas B4112 per se at 100 ng/ml inhibited parasite growth by 27 percent. However, B4112 (100 ng/ml) increased the sensitivity of this strain of *P. falciparum* to 125 nM chloroquine from 33 to 100 percent as is seen in FIG. 1 of the accompanying drawings.

Conclusions

In this experiment B4112 and chloroquine clearly interacted synergistically.

Example 4

DIRECT ANTIMALARIAL ACTIVITY OF THE RIMINOPHENAZINE

To investigate the direct antimalarial activity of the riminophenazines B669, B4100, B4103, B4112, B4121, B4158 and B4169 against a laboratory strain of *P. falciparum* the following experiment was done:

Methods

A laboratory strain of *P. falciparum* (RB-1; obtained from Dr B L Sharp, National Malaria Research Programme, MRC, Durban) was maintained.

For these experiments malaria cultures of haematocrit 5.0% and initial parasitemia 2.0% were used. The malaria infected erythrocytes (ring stage) were incubated in microtitre plates with serial dilutions of B669, B4100, B4103, B4112, B4121, B4158 and B4169 (0.125–2 μg/ml) for 48 hours and processed for analysis on the flow cytometer as described in Example 3.

Results

The effects of B669, B4100, B4103, B4112, B4121, B4158 and B4169 on the growth of *P. faliparum* can be seen from FIG. 2 of the accompanying drawings. B669, B4103, B4112 and B4158 inhibited the growth of this strain of the malarial parasite by more than 50% at a concentration of 0.5 μg/ml with the order of activity B4158>B4112>B4103>B669 at this concentration as can be seen from FIG. 2 of the accompanying drawings.

Conclusions

These results indicate once again the potential use of the riminophenazines, especially B4158 and B4112, in the treatment of prophylaxis of chloroquine resistant malaria.

Example 5

Some compositions of the invention are made up as follows:

| CAPSULES | mg/capsule |
|---|---|
| Riminophenazine | 100–2000 mg |
| Diluent/Disintegrant | 5–200 mg |
| Glidants | 0–15 mg |
| Disintegrants | 0–20 mg |
| TABLETS | mg/tablet |
| Riminophenazine | 100–2000 mg |
| Diluent | 5–200 mg |
| Disintegrant | 2–50 mg |
| Binder | 5–100 mg |
| Lubricant | 2–20 mg |
| SYRUP | mg/10 ml |
| Riminophenazine | 100–2000 mg |
| Solvents, solubilisers, stabilisers | 5–500 mg |
| Colouring agents | 0,5–150 mg |
| Preservatives/Antioxidants | 1–150 mg |
| Flavours | 5–200 mg |
| INTRAVENOUS | |
| Riminophenazine | 100–2000 mg |
| Alkali/buffer, Isotonically agents | 5–100 µg |
| Stabilisers, solubilisers | 0–100 µg |

We claim:

1. A method for the prophylactic and the therapeutic treatment of malaria infections of the human or animal body comprising administering an effective amount of a riminophenazine to the human or animal body in need thereof, the riminophenazine having the general formula:

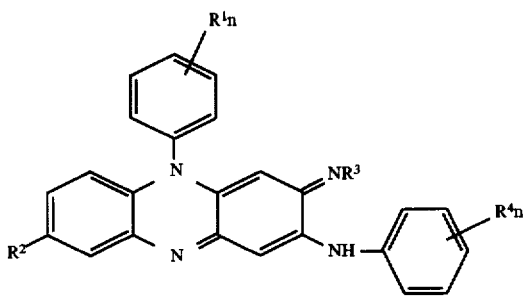

wherein:

$R^1$ and $R^4$ are selected from hydrogen atoms, halogen atoms, alkyl, alkoxy and trifluoromethyl radicals, $R^2$ is selected from hydrogen and halogen atoms, $R^3$ is selected from hydrogen atoms, alkyl, N,N-dialkylamino alkyl, cycloalkyl, cycloalkylalkyl, 4-piperidyl-,4-(2,2,6,6-tetramethylpiperidyl)- and 4'-(N-benzylpiperidyl)-, wherein the alkyls are lower, and n is 1, 2 or 3, provided that when $R^3$ is isopropyl, $R^1$ and $R^4$ are not both chlorine.

2. The method recited in claim 1, wherein $R^3$ is a 2',2',6',6'-tetramethyl-4-piperidyl radical.

3. The method recited in claim 1, wherein there are at least two substituents in each of the phenyl rings in the 3-amino and 10-positions of the phenazine ring of the compound.

4. The method recited in claim 1, wherein there is at least one fluorine atom in each of the phenyl rings in the 3-amino and 10-positions of the phenazine ring of the compound.

5. The method recited in claim 1, wherein the compound is N,5-bis(3-chlorophenyl)-3,5,-dihydro-3-[(2',2',6',6'-tetramethyl-4-piperidyl)-imino]-2-phenazinamine.

6. The method recited in claim 1, wherein the compound is N,5-bis(4-isopropylphenyl)-3,5-dihydro-3[(2',2',6',6'-tetramethyl-4-piperidyl)-imino]-2-phenazinamine.

* * * * *